United States Patent [19]

Schmitt et al.

[11] Patent Number: 4,520,023

[45] Date of Patent: May 28, 1985

[54] 3-(3-IODOPROPARGYL)-BENZO-1,2,3-TRIAZIN-4-ONES, AND THEIR USE IN MICROBICIDAL AGENTS

[75] Inventors: Hans-Georg Schmitt, Leverkusen; Wilfried Palus; Hermann Genth, both of Krefeld, all of Fed. Rep. of Germany

[73] Assignee: Bayer Aktiengesellschaft, Leverkusen, Fed. Rep. of Germany

[21] Appl. No.: 549,338

[22] Filed: Nov. 4, 1983

[30] Foreign Application Priority Data

Nov. 9, 1982 [DE] Fed. Rep. of Germany ....... 3241265

[51] Int. Cl.$^3$ .................. C07D 253/08; A61K 31/53
[52] U.S. Cl. ................................. 514/241; 544/183
[58] Field of Search ...................... 544/183; 424/249

[56] References Cited

U.S. PATENT DOCUMENTS 3,316,262 4/1967 Hasspacher et al. ............... 544/183
3,446,797 5/1969 Focella et al. .................. 260/239.3

FOREIGN PATENT DOCUMENTS 2209470 9/1972 Fed. Rep. of Germany .
2910220 9/1979 Fed. Rep. of Germany .

OTHER PUBLICATIONS

Chemical Abstracts, Band 97, Nr. 3, 19, Jul. 1982, p. 713, Nr. 23779c, Columbus, Ohio, US & CS-A-194 354 (Skacani, Ivan et al.) 2/15/82.

Primary Examiner—John M. Ford
Attorney, Agent, or Firm—Sprung Horn Kramer & Woods

[57] ABSTRACT

The new 3-(3-iodopropargyl)-benzo-1,2,3-triazin-4-ones can be prepared by reacting benzo-1,2,3-triazin-4-ones with a propargyl compound. The new compounds can be used as active compounds in microbicidal agents.

16 Claims, No Drawings

3-(3-IODOPROPARGYL)-BENZO-1,2,3-TRIAZIN-4-ONES, AND THEIR USE IN MICROBICIDAL AGENTS

The invention relates to new 3-(3-iodopropargyl)-benzo-1,2,3-triazin-4-ones, processes for their preparation and their use in microbicidal agents.

The new 3-(3-iodopropargyl)-benzo-1,2,3-triazin-4-ones correspond to the formula

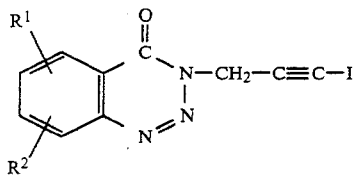

in which $R^1$ denotes hydrogen, lower alkyl, halogen, cyano, nitro, lower alkoxy, aryloxy, lower alkylthio, arylthio, $C_1$–$C_{10}$-alkoxycarbonyl, lower alkylsulphonyl or arylsulphonyl and $R^2$ denotes hydrogen, lower alkyl or halogen.

In this context, according to the invention, lower alkyl can be a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl. Preferred lower alkyl radicals are the methyl and ethyl radicals.

In this context, according to the invention, lower alkoxy can be a straight-chain or branched hydrocarbon radical which has 1 to about 6 carbon atoms and is bonded via oxygen. The following lower alkoxy radicals may be mentioned as examples: methoxy, ethoxy, propoxy, isopropoxy, butoxy, isobutoxy, pentoxy, isopentoxy, hexoxy and isohexoxy. The methoxy and ethoxy groups are preferred.

In this context, according to the invention, aryloxy can be an aromatic radical from the benzene series which has 6 to 18 carbon atoms and is bonded via oxygen. The following aryloxy radicals may be mentioned as examples: phenoxy and naphthoxy.

The phenoxy radical is preferred.

In this context, according to the invention, lower alkylthio can be a straight-chain or branched hydrocarbon radical which has 1 to about 6 carbon atoms and is bonded via sulphur. The following lower alkylthio radicals may be mentioned as examples: methylthio, ethylthio, propylthio, isopropylthio, butylthio, isobutylthio, pentylthio, isopentylthio, hexylthio and isohexylthio. The methylthio and ethylthio radicals are preferred.

In this context, according to the invention, arylthio can be an aromatic radical from the benzene series which has 6 to 18 carbon atoms and is bonded via sulphur. The following arylthio radicals may be mentioned as examples: phenylthio, naphthylthio, chlorophenylthio and tolylthio.

The phenylthio radical is preferred.

In this context, according to the invention, alkoxycarbonyl can be a radical of the formula

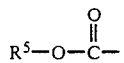

in which $R^5$ is a straight-chain or branched hydrocarbon radical with 1 to 10, preferably 1 to 6, carbon atoms.

The following alkoxycarbonyl radicals may be mentioned as examples: methoxycarbonyl, ethoxycarbonyl, propoxycarbonyl, isopropoxycarbonyl, butoxycarbonyl, isobutoxycarbonyl, pentoxycarbonyl and hexoxycarbonyl.

The preferred alkoxycarbonyl radical is the methoxycarbonyl radical.

In this context, according to the invention, lower alkylsulphonyl can be a sulphonyl radical which is substituted by a straight-chain or branched hydrocarbon radical with 1 to about 6 carbon atoms. The following lower alkylsulphonyl radicals may be mentioned as examples: methylsulphonyl, ethylsulphonyl, propylsulphonyl and butylsulphonyl.

The preferred alkylsulphonyl radical is the methylsulphonyl radical.

In this context, according to the invention, arylsulphonyl can be a sulphonyl radical which is substituted by an aromatic radical from the benzene series with 6 to 18 carbon atoms. The following radicals may be mentioned as examples: phenylsulphonyl, naphthylsulphonyl, tolylsulphonyl and chlorophenylsulphonyl.

The preferred arylsulphonyl radical is the phenylsulphonyl radical.

According to the invention, 3-(3-iodopropargyl)-benzo-1,2,3-triazin-4-ones of the formula

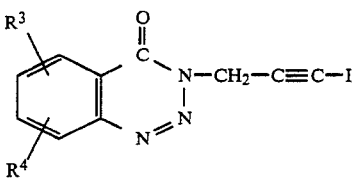

in which $R^3$ denotes hydrogen, lower alkyl, fluorine, chlorine, bromine or nitro and $R^4$ denotes hydrogen, lower alkyl or chlorine, are preferred.

The following 3-(3-iodopropargyl)-benzo-1,2,3-triazin-4-ones may be mentioned as examples: 3-(3-iodopropargyl)-benzo-1,2,3-triazin-4-one, 5-chloro-3-(3-iodopropargyl)-benzo1,2,3-triazin-4-one, 6-chloro-3-(3-iodopropargyl)-benzo-1,2,3-triazin-4-one, 7-chloro-3-(3-iodopropargyl)-benzo-1,2,3-triazin-4-one, 7-fluoro-3-(3-iodopropargyl)-benzo-1,2,3-triazin-4-one, 7-bromo-3-(3-iodopropargyl)-benzo-1,2,3-triazin-4-one, 6,8-dichloro-3-(3-iodopropargyl)-benzo-1,2,3-triazin-4-one, 6,8-dibromo-3-(3-iodopropargyl)-benzo-1,2,3-triazin-4-one, 3-(3-iodopropargyl)-6-nitro-benzo-1,2,3-triazin-4-one and 3-(3-iodopropargyl)-5-methyl-benzo-1,2,3-triazin-4-one.

The new 3-(3-iodopropargyl)-benzo-1,2,3-triazin-4-ones can be prepared by a process in which benzo-1,2,3-triazin-4-ones of the formula

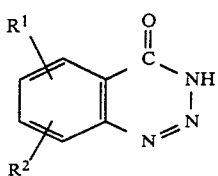

in which
R¹ and R² have the abovementioned meaning, are reacted with a propargyl compound of the formula $$X^1-CH_2-C\equiv C-I$$

in which
X¹ represents halogen, alkylsulphonyloxy or arylsulphonyloxy,
in the presence of a base.

The process according to the invention can be illustrated with the aid of the following equation:

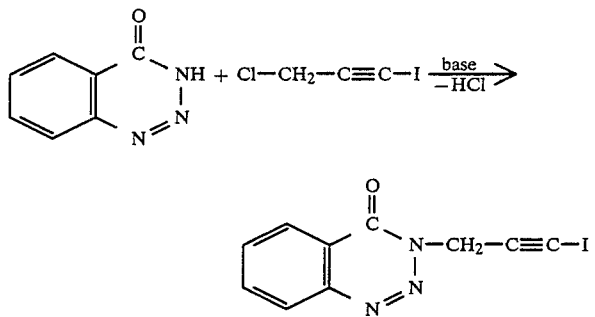

In another embodiment of the process according to the invention, salts of benzo-1,2,3-triazin-4-ones, of the formula

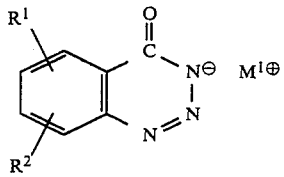

in which
R¹ and R² have the abovementioned meaning and
M¹⊕ represents a metal ion, are reacted with a propargyl compound of the formula $$X^1-CH_2-C\equiv C-I$$

in which
X¹ has the abovementioned meaning.

This embodiment of the process according to the invention can be illustrated by the following equation:

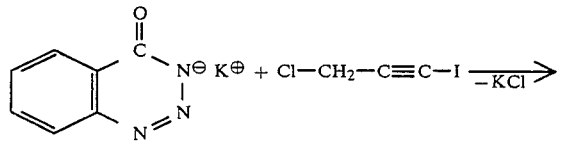

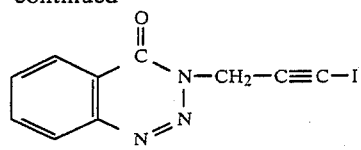

Benzo-1,2,3-triazin-4-ones for the process according to the invention are known per se (for example J. Org. Chem. 26, 619 (1961)). They can be prepared, for example, by preparing the isatoic anhydrides starting from the corresponding anthranilic acids with phosgene in the presence of an acid-binding agent and splitting these anhydrides to anthranilamides with ammonia. The anthranilamides can be converted into the benzo-1,2,3-triazin-4-ones by diazotization with sodium nitrite in aqueous hydrochloric acid solution.

Preferred salts of benzo-1,2,3-triazin-4-ones are generally the alkali metal salts, in particular the sodium and potassium salts. These salts can be prepared from the benzo-1,2,3-triazin-4-ones by adding a corresponding base, for example sodium hydroxide or potassium hydroxide, in aqueous, alcoholic or ethereal dilution.

Benzo-1,2,3-triazin-4-ones of the formula

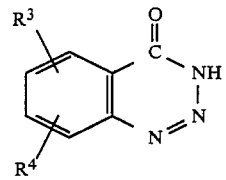

in which
R³ and R⁴ have the abovementioned meaning, and salts of benzo-1,2,3-triazin-4-ones, of the formula

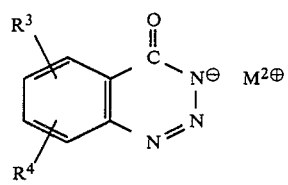

in which
R³ and R⁴ have the abovementioned meaning and
M²⁺ represents an alkali metal or alkaline earth metal ion,
are preferred for the process according to the invention.

The following benzo-1,2,3-triazin-4-ones may be mentioned as examples: benzo-1,2,3-triazin-4-one, 5-chloro-benzo-1,2,3-triazin-4-one, 6-chloro-benzo-1,2,3-triazin-4-one, 7-chloro-benzo-1,2,3-triazin-4-one, 7-fluoro-benzo-1,2,3-triazin-4-one, 7-bromo-benzo-1,2,3-triazin-4-one, 6-nitro-benzo-1,2,3-triazin-4-one, 6,8-dichloro-benzo-1,2,3-triazin-4-one, 6,8-dibromo-benzo-1,2,3-triazin-4-one and 5-methyl-benzo-1,2,3-triazin-4-one.

Salts of benzo-1,2,3-triazin-4-ones which may be mentioned are the sodium and potassium salts of the above compounds.

Iodopropargyl compounds of the process according to the invention are likewise known per se, and can be prepared, for example, by reacting 3-chloro-propine with iodine in aqueous/alkaline solution at 0° to 5° C. (J. Am. Chem. Soc. 77, 176 (1955)) or they are obtained by reacting 3-iodopropargyl alcohol with benzenesulphonyl chloride (German Offenlegungsschrift No. 2,910,220).

The following iodopropargyl compounds may be mentioned as examples: 3-chloro-1-iodopropine, 3-bromo-1-iodopropine, 1,3-diiodopropine, 3-iodopropargyl benzenesulphonate, 3-iodopropargyl 4-toluenesulphonate and 3-iodopropargyl methanesulphonate.

Iodopropargyl compounds of the formula

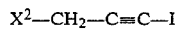

$$X^2-CH_2-C\equiv C-I$$

in which $X^2$ represents chlorine, bromine or phenylsulphonyloxy, are preferred for the process according to the invention.

3-Chloro-1-iodopropine and 3-bromo-1-iodopropine are particularly preferred.

The reaction of benzo-1,2,3-triazin-4-ones with iodopropargyl compounds is carried out in the presence of bases which bond the hydrogen halide or sulphonic acid formed. Bases which may be mentioned are alkali metal carbonates and alkaline earth metal carbonates, and tertiary amines. In this context, alkali metal carbonates are essentially sodium and potassium carbonate. In this context, alkaline earth metal carbonates are essentially magnesium and calcium carbonate. In this context, tertiary amines are essentially amines substituted by straight-chain or branched lower alkyl radicals (1 to about 6 carbon atoms), such as triethylamine.

The process according to the invention is in general carried out in the temperature range from 20° to 100° C., preferably from 40° to 80° C.

The process according to the invention is in general carried out under normal pressure. However, it is also possible to carry out the process according to the invention under a reduced or increased pressure, for example in the pressure range from 0.5 to 5 bar.

In general, the benzo-1,2,3-triazin-4-one, or its salt, and the iodopropargyl compound are employed in approximately equimolar amounts for the process according to the invention. However, it is also possible to employ one or other of the components in excess.

The process according to the invention can be carried out in the presence of a solvent or diluent. Solvents or diluents for the process according to the invention are compounds which do not change under the conditions according to the invention. Examples which may be mentioned are alcohols, such as ethanol, propanol and butanol, ethers, such as dioxane and tetrahydrofuran, hydrocarbons, such as toluene, chlorohydrocarbons, such as chloroform, ketones, such as acetone, and amides, such as dimethylformamide.

The process according to the invention can be carried out, for example, as follows:

Where relevant, the benzo-1,2,3-triazin-4-one is dissolved or suspended in a solvent and the base is added. The iodopropargyl compound is then added dropwise at the reaction temperature. When the reaction has ended, the reaction mixture is introduced into water. The 3-(3-iodopropargyl)-benzo-1,2,3-triazin-4-one compound precipitates and can be separated off and purified in the customary manner.

The 3-(3-iodopropargyl)-benzo-1,2,3-triazin-4-ones according to the invention can be used as active compounds for combating microorganisms, in particular, in industrial materials.

Industrial materials are non-living materials which have been prepared for use in industry. Industrial materials which are to be preserved, by the active compound according to the invention, from microbial change and destruction can be, for example, adhesives, sizes, papers and cardboards, textiles, leather, wood, paints, building materials, rubber and articles made of plastic, cooling lubricants and other materials which can be decomposed by microorganisms. In the context of the materials to be preserved, components of production plants, for example cooling water circulations, which may be impaired by microorganisms may also be mentioned. Industrial materials mentioned as preferred in the context of the present invention are articles made of wood, and paints and coating agents.

Examples of microorganisms which can effect degradation or change in the industrial materials are fungi, bacteria, yeasts, algae and slime organisms. The substances according to the invention preferentially act against fungi.

Microorganisms of the following genera may be mentioned as examples: Alternaria, such as *Alternaria tenius*, Aspergillus, such as *Aspergillus niger*, Chaetomium, such as *Chaetomium globosum*, Coniophora, such as *Coniophora cerebella*, Lentinus, such as *Lentinus tigrinus*, Penicillium, such as *Penicillium glaucum*, Polyporus, such as *Polyporus versicolor*, Aureobasidium, such as *Aureobasidium pullulans* and Sclerophoma, such as *Sclerophoma pityophila*.

The active compounds according to the invention can be converted to the customary formulations, such as solutions, emulsions, suspensions, powders, pastes and granules, depending on their field of use. These formulations can be prepared in a known manner, for example by mixing the active compounds with an extender consisting of a liquid solvent and/or solid carriers, if necessary using surface-active agents, such as emulsifiers and/or dispersing agents, it being possible, for example, if aqueous extenders are used, for organic solvents optionally to be used as auxiliaries.

Solid carriers which are added during the preparation of the finished use forms of the active compound can be, for example, fine-particled aluminum oxides, silicates, carbonates, iron oxides, gypsum or wood flour.

Surface-active agents can be commercially available emulsifiers, such as aryl- or alkyl-sulphonates, ethoxylated alkylphenols, fatty alcohols or alkylamines, or dispersing agents, such as polycarboxylic acid esters, polyvinyl alcohol, lignin, sulphite waste liquors or methylcellulose.

Organic solvents for the active compounds can be, for example, alcohols, such as lower aliphatic alcohols, preferably ethanol and isopropanol, or benzyl alcohol, ketones, such as acetone or methyl ethyl ketone, liquid hydrocarbons, such as benzine fractions, and chlorinated hydrocarbons, such as 1,2-dichloroethane.

The use forms of the microbicidal agent according to the invention in general contain 5 to 99.5% by weight, preferably 20 to 90% by weight, of the 3-(3-iodopropargyl)-benzo-1,2,3-triazin-4-one as the active compound. The use concentration of the active compounds according to the invention which is required for preserving industrial materials depends on the nature and occurrence of the microorganisms to be combated and on the composition of the material to be preserved. The optimum amount used can be determined by series of tests. In general, the use concentrations are in the range from 0.001 to 5% by weight, preferably 0.05 to 1% by weight, based on the material to be preserved.

The active compounds according to the invention can be present in the formulations as mixtures with other known inorganic or organic fungicides and/or insecticides. The following active compounds may be mentioned as examples: phenol derivatives, compounds which split off formaldehyde, dithiocarbonates, benzimidazolylcarbamates, thiazolylbenzimidazole, isothiazolone and benzisothiazolone derivatives, trihalogenomethylthio compounds, tetrachloroisophthalic acid dinitrile, mercaptobenzothiazole and mercaptopyridine.

The 3-(3-iodopropargyl)-benzo-1,2,3-triazin-4-one active compound according to the invention is distinguished by a high activity in comparison with similar active compounds. In particular, it exhibits a high stability in alkaline media, which means its applicability as a microbicide for the preservation of industrial material is substantially broadened.

PREPARATION

EXAMPLE 1

8.38 g (0.038 mol) of the potassium salt of 7-chlorobenzo-1,2,3-triazin-4-one are suspended in 150 ml of dimethylformamide. 8 g (0.0399 mol) of 3-chloro-1-iodopropine are added dropwise at 20° C. Stirring is continued for about 8 hours and the reaction mixture is then introduced into 600 ml of water; the crystals which have precipitated are filtered off with suction and dried in air. For purification, the product is dissolved in dioxane and the solution is stirred for a short time, with the addition of a little active charcoal, and, after filtration, is concentrated. 7 g (53.5% of theory) of 7-chloro-3-(3-iodopropargyl)-benzo-1,2,3-triazin-4-one are obtained as slightly yellow crystals of melting point 157°–159° C.

EXAMPLES 2 TO 5

The following compounds are prepared in the same manner as in Example 1:
2. 3-(3-Iodopropargyl)-benzo-1,2,3-triazin-4-one; melting point: 142°–144° C.,
3. 3-(3-Iodopropargyl)-6-nitro-benzo-1,2,3-triazin-4-one; melting point: 178°–180° C.,
4. 6-Chloro-3-(3-iodopropargyl)-benzo-1,2,3-triazin-4-one; melting point: 172°–175° C. and
5. 6,8-Dichloro-3-(3-iodopropargyl)-benzo-1,2,3-triazin-4-one; melting point: 172°–174° C. (from acetone).

USE EXAMPLES

The following active compounds are used:
(A) 3-(3-Iodopropargyl)-benzo-1,2,3-triazin-4-one
(B) 3-(3-Iodopropargyl)-6-nitro-benzo-1,2,3-triazin-4-one
(C) 3-(3-Iodopropargyl)-7-chloro-benzo-1,2,3-triazin-4-one
(D) For comparison: iodopropargyl N-butyl-carbamate ("Polyphase Antimildew" from Messrs. Troy Chem. Corp. USA).

EXAMPLE 6

To demonstrate the activity against fungi, the minimum inhibitory concentrations (MIC) of active compounds according to the invention are determined:

Active compounds according to the invention are added, in concentrations of 0.1 mg/liter to 5,000 mg/liter, to an agar prepared from beerwort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which no growth at all by the species of microbe used takes place; the MIC values are summarized in the tables below.

TABLE I

| | MIC value [mg/liter] | | | |
| | Active compound | | | |
| Test organisms | A | B | C | D (comparison) |
|---|---|---|---|---|
| Alternaria tenuis | 5 | | | |
| Aspergillus niger | 5 | <20 | <20 | 80 |
| Aureobasidium pullulans | 5 | | | |
| Chaetomium globosum | <20 | <20 | <20 | 60 |
| Coniophora cerebella | 0.5 | | | |
| Lentinus tigrinus | 2 | | | |
| Penicillium glaucum | 5 | <20 | <20 | 40 |
| Sclerophoma pityophila | 3.5 | | | |
| Trichoderma viride | 10 | | | 140 |

EXAMPLE 7 (ACTION AGAINST SLIME ORGANISMS)

Compounds according to the invention, dissolved in acetone, are used in concentrations of in each case 0.1 to 100 mg/liter in Allens nutrient solution (Arch. Mikrobiol. 17, 34 to 53 (1952)) containing, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infected with slime organisms (about $10^6$ germs/ml) which have been isolated from the spinning water circulations used in the preparation of polyamide. Nutrient solutions containing the minimum inhibitory concentration (MIC) or larger concentrations of active compound are still completely clear after culturing at room temperature for 3 weeks, that is to say the heavy reproduction of the microbes and formation of slime noticeable in active compound-free nutrient solutions after 3 to 4 days does not take place.

TABLE II

| MIC value [mg/liter] | |
|---|---|
| Active compound | MIC in mg/liter |
| A | 5 |
| B | 20 |
| C | 30 |

EXAMPLE 8

Testing of Paint Films for Resistance to Mould

The test is carried out in accordance with Report 219 of the Defense Standards Laboratories Maibyrnong-/Australia, as follows: smooth cardboard is coated on both sides with the product to be tested and is dried at room temperature for 8 days. For ageing, part of the coating is kept in running water at 24° C. for 24 hours, part is aerated with fresh air of 40° to 60° C. for 8 days, and part is exposed to a dry Xenon test for 110 hours. 5×5 cm sections of the test pieces thus treated are placed individually in Petri dishes on a glucose nutrient medium, and are contaminated with a spore suspension of the following fungi: *Aspergillus niger, Aureobasidium pullulans, Alternaria speciales, Penicillium citrinum, Stachybotrys atra, Paecilomyces varioti, Cladosporium herbarum, Aspergillus ustus* or *Aspergillus flavus*.

The contaminated dishes are kept at 28°–30° C. and 90–95% relative atmospheric humidity, and are evaluated after 3 weeks. Paint films are regarded as mould-resistant if the test pieces remain free from fungi after this test.

A commercially available, alkaline emulsion paint based on polyvinyl acetate is tested for mould resistance by the test method described above.

Samples of the paint containing 1.5 to 2% (or more) of 3-(3-iodopropargyl)-benzo-1,2,3-triazin-4-one, based on the total solids content, give very good mould-resistant paint films; this is even the case if the paint films have first been subjected to the abovementioned stresses.

What is claimed is:

1. 3-(3-iodopropargyl)-benzo-1,2,3-triazin-4-one of the formula

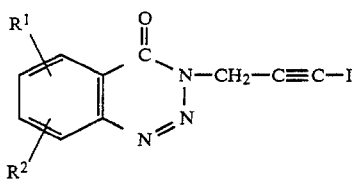

in which
R$^1$ is hydrogen, lower alkyl, halogen, cyano, nitro, lower alkoxy, aryloxy having 6–18 carbon atoms, lower alkylthio, arylthio having 6–18 carbon atoms, C$_1$–C$_{10}$-alkoxycarbonyl, lower alkylsulphonyl or arylsulphonyl having 6–18 carbon atoms, and
R$^2$ is hydrogen, lower alkyl or halogen.

2. 3-(3-Iodopropargyl)-benzo-1,2,3-triazin-4-one according to claim 1, of the formula

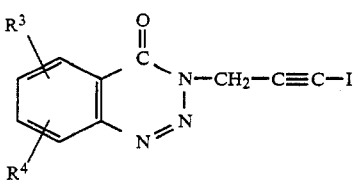

in which
R$^3$ is hydrogen, lower alkyl, fluorine, chlorine, bromine or nitro and
R$^4$ is hydrogen, lower alkyl or chlorine.

3. A compound according to claim 1 which is 3-(3-iodopropargyl)-benzo-1,2,3-triazin-4-one.

4. A compound according to claim 1 which is 3-(3-iodopropargyl)-6-nitro-benzo-1,2,3-triazin-4-one.

5. A compound according to claim 1 which is 6-chloro-3-(3-iodopropargyl)-benzo-1,2,3-triazin-4-one.

6. A compound according to claim 1 which is 6,8-dichloro-3-(3-iodopropargyl)-benzo-1,2,3-triazin-4-one.

7. A compound according to claim 1 which is 3-(3-iodopropargyl)-7-chloro-benzo-1,2,3-triazin-4-one.

8. A 3-(3-iodopropargyl)-benzo-1,2,3-triazin-4-one according to claim 1 which is 5-chloro-(3-iodopropargyl)-benzo-1,2,3-triazin-4-one.

9. A 3-(3-iodopropargyl)-benzo-1,2,3-triazin-4-one according to claim 1 which is 7-chloro-3-(3-iodopropargyl)-benzo-1,2,3-triazin-4-one.

10. A 3-(3-iodopropargyl)-benzo-1,2,3-triazin-4-one according to claim 1 which is 7-fluoro-3-(3-iodopropargyl)-benzo-1,2,3-triazin-4-one.

11. A 3-(3-iodopropargyl)-benzo-1,2,3-triazin-4-one according to claim 1 which is 7-bromo-3-(3-iodopropargyl)-benzo-1,2,3-triazin-4-one.

12. A 3-(3-iodopropargyl)-benzo-1,2,3-triazin-4-one according to claim 1 which is 6,8-dibromo-3-(3-iodopropargyl-benzo-1,2,3-triazin-4-one.

13. A 3-(3-iodopropargyl)-benzo-1,2,3-triazin-4-one according to claim 1 which is 3-(3-iodopropargyl)-5-methyl-benzo-1,2,3-triazin-4-one.

14. A microbicidal composition comprising a microbicidally effective amount of 3-(3-iodopropargyl)-benzo-1,2,3-triazin-4-one of the formula

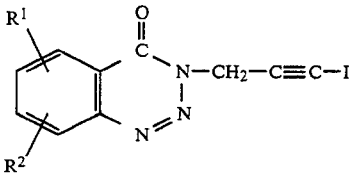

in which
R$^1$ is hydrogen, lower alkyl, halogen, cyano, nitro, lower alkoxy, aryloxy having 6–18 carbon atoms, lower alkylthio, arylthio having 6–18 carbon atoms, C$_1$–C$_{10}$-alkoxycarbonyl, lower alkylsulphonyl or arylsulphonyl having 6–18 carbon atoms, and
R$^2$ is hydrogen, lower alkyl or halogen and a microbiologically compatible diluent.

15. A composition according to claim 14 wherein said 3-(3-iodopropargyl)-benzo-1,2,3-triazin-4-one is present in the composition in an amount of 0.5 to 99.5% by weight.

16. A microbicidal composition according to claim 14 wherein said 3-(3-iodopropargyl)-benzo-1,2,3-triazin-4-one is one of the formula

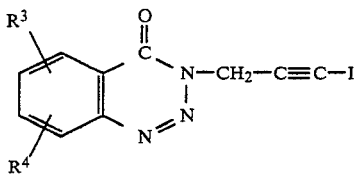

wherein R$^3$ is hydrogen, lower alkyl, flourine, chlorine, bromine or nitro and R$^4$ is hydrogen, lower alkyl or chlorine.

* * * * *